United States Patent
Rack et al.

(10) Patent No.: US 12,178,462 B2
(45) Date of Patent: Dec. 31, 2024

(54) SURGICAL INSTRUMENT

(71) Applicant: MORPHEUS AG, Spaichingen (DE)

(72) Inventors: Timo Rack, Rietheim-Weilheim (DE); Heiko Blessing, Durchhausen (DE)

(73) Assignee: MORPHEUS AG, Spaichingen (DE)

( * ) Notice: Subject to any disclaimer, the term of this patent is extended or adjusted under 35 U.S.C. 154(b) by 674 days.

(21) Appl. No.: 17/275,487

(22) PCT Filed: May 9, 2019

(86) PCT No.: PCT/EP2019/061980
§ 371 (c)(1),
(2) Date: Mar. 11, 2021

(87) PCT Pub. No.: WO2020/052816
PCT Pub. Date: Mar. 19, 2020

(65) Prior Publication Data
US 2022/0079612 A1 Mar. 17, 2022

(30) Foreign Application Priority Data
Sep. 12, 2018 (DE) .................. 102018122237.8

(51) Int. Cl.
*A61B 17/29* (2006.01)
*A61B 17/00* (2006.01)

(52) U.S. Cl.
CPC .. *A61B 17/2909* (2013.01); *A61B 2017/0042* (2013.01); *A61B 2017/2913* (2013.01); *A61B 2017/2919* (2013.01)

(58) Field of Classification Search
CPC ............ A61B 17/2912; A61B 17/2909; A61B 17/1608; A61B 2017/2913; A61B 2017/2919; A61B 2017/0042; B25B 7/00; B25B 7/12; B25B 23/16
See application file for complete search history.

(56) References Cited

U.S. PATENT DOCUMENTS

| | | | |
|---|---|---|---|
| 5,052,243 A | 10/1991 | Tepic | |
| 5,307,976 A * | 5/1994 | Olson | A61B 17/07207 227/175.3 |
| 5,499,548 A | 3/1996 | Keller | |
| 2010/0030029 A1 | 2/2010 | Markham | |
| 2018/0000514 A1 | 1/2018 | Koller | |

OTHER PUBLICATIONS

International Search Report from corresponding PCT Patent Application No. PCT/EP2019/061980 dated Jul. 31, 2019.

\* cited by examiner

*Primary Examiner* — Katherine M Shi
*Assistant Examiner* — Mohammed S Adam
(74) *Attorney, Agent, or Firm* — Grogan, Tuccillo & Vanderleeden LLP

(57) ABSTRACT

The invention relates to a surgical instrument with a grip area, which has a first handle part, which is fixed in the position of use, and a second handle part, which can be moved relative to the first handle part along an adjustment direction, wherein a ratio between a first distance between the first handle part and the second handle part and a second distance between the first handle part and the second handle part is constant or almost constant in the direction of the first handle part, at least over a partial area of the actuating path, during a movement of the second handle part.

10 Claims, 4 Drawing Sheets

SURGICAL INSTRUMENT

CROSS-REFERENCE TO RELATED APPLICATIONS

This application is a national stage of International Application No. PCT/EP2019/061980 filed on May 9, 2019, which claims priority to German Patent Application No. 102018122237.8 filed on Sep. 12, 2018, all of which are hereby incorporated by reference in their entireties.

FIELD OF THE INVENTION

The invention relates to a surgical instrument with a grip area which has a first handle part which is fixed in the position of use and a second handle part which can be moved in an adjustment direction relative to the first handle part. In particular, the surgical instrument can be configured for tissue separation, for example as a tissue punch. Known tissue punches are, for example, so-called Kerrison or Rongeur punches.

US 2018/0000514 A1 relates to a shaft instrument for surgical purposes, with a shaft part that is firmly connected to a shaft handle at one end, and with a sliding part that is mounted displaceably relative to the shaft part in its longitudinal direction and is operatively connected to a pretensioned handle at one end in such a way that the sliding part can be displaced against the pretension by actuating the handle. The handle has a coupling section in which two lever arms of the handle are coupled to one another at a distance from one another.

Similar surgical instruments are known from US 2010/0030029 A1, U.S. Pat. No. 5,052,243 A, and 5,499,548 A.

Typical surgical instruments of the type mentioned at the outset have the disadvantage that a user, who can be a surgeon, for example, tires relatively quickly during time-consuming work with the surgical instrument. While working with the surgical instrument, the user has to operate the grip area several times by means of the user's hand strength, which after a while can lead to the arm and hands becoming sore because the muscles tire. This affects the accuracy of the surgeon's work. For example, the instruments are used to remove bone material or intervertebral disc material in the vicinity of nerves on the spine, so that particularly precise actuation of the instrument is important in order to avoid injuries to the nerves. Users often try to remedy this by changing hands to operate the surgical instrument.

BACKGROUND OF THE INVENTION

The object is therefore to create a surgical instrument of the type mentioned at the outset, in which the disadvantages mentioned have been eliminated and which has an ergonomic grip area which makes a user less tired when using the surgical instrument.

The object is achieved according to the invention by the features of claim 1. In particular, a surgical instrument of the type mentioned above is proposed to achieve the object, characterized in that at least two points of articulation are formed offset to each other on the second handle part, through which an adjustment direction of the second handle part is defined relative to the first handle part. The configuration according to the invention makes it possible for a user to be able to work longer with the surgical instrument, since the user is less quickly exhausted than with previously known instruments. This is due to the fact that the movable handle part is not adjusted around a single point of articulation or pivot point, but rather around two points of articulation arranged offset from one another. It is thus possible that by actuating the second handle part, the second handle part can be moved towards the first handle part in a kind of parallel movement or elliptical movement or pivoting movement and not, as usual, in a circular movement around a single point of articulation. In most surgical instruments of the type mentioned at the outset, when moving along a circular path, the little finger of the hand is in contact for the longest with the lever formed by the movable handle part. These previously known instruments usually have a V-shaped grip area. The consequence of this is that the little finger has to be used to exert the greatest amount of force in order to adjust the movable handle part. Ultimately, this can lead to more rapid muscle fatigue in the user. However, the geometry of the surgical instrument of the type mentioned at the outset cannot be fundamentally changed, so that the little finger must continue to be placed closest to the free end of the movable handle part. Due to the parallel or almost parallel alignment of the two handle parts over at least part of the actuation path and/or the elliptical relative movement between the handle parts in the surgical instrument according to the invention, a significantly more uniform transmission of the hand force is made possible. The adjustment direction can thus run in a more straight line, in particular almost in a straight line, or on an elliptical path, at least over a first half of an actuation path.

SUMMARY OF THE INVENTION

A ratio between a first distance between the first and the second handle part and a second distance between the first and the second handle part can thus be constant or almost constant during a movement of the second handle part in the direction of the first handle part, at least over the first half of an actuation path. The first distance and the second distance can extend parallel to one another. Alternatively or additionally, the first distance and the second distance can be parallel to a shaft receptacle and/or a slide rail of the surgical instrument. Alternatively or additionally, a distance between the first distance and the shaft receptacle and a distance between the second distance and the shaft receptacle can be of different sizes. As an alternative or additionally, the distances can each extend between a hand contact surface on the first handle part and a hand contact surface on the second handle part.

Advantageous refinements of the invention are described below which, alone or in combination with the features of other refinements, can optionally be combined with the features according to claim 1.

According to one embodiment, the adjustment direction of the second handle part can be determined by at least two guide elements, the two guide elements each being connected to the first handle part via a point of articulation and to the second handle part via a point of articulation, their points of articulation being arranged offset to one another on the first handle part, and their points of articulation being arranged offset to one another on the second handle part. The points of articulation can be, for example, mounted pivot axes. In particular, they may be adjustable only in one degree of freedom and/or pivot axes mounted in a pivot bearing. This has the advantage that a particularly simple guide for the movable second handle part is formed, which consists of as few parts as possible. The guide elements can be designed as guide levers, for example. For example, at least one of the guide levers or all of the guide levers can be designed to be rigid, that is to say in particular inflexible, in order to enable particularly good guidance. A point of articulation within the meaning of the application can be, for example, a pivot axis guided in a pivot bearing. The pivot axis can be formed, for example, on the handle part and/or on the guide element and/or on the drive element.

In order to be able to increase a stroke of the surgical instrument even further without having to widen the distance between the two handle parts in a rest position, the surgical instrument can have a drive element which is connected to the second handle part via a bearing point and/or which is connected to the first handle part via a bearing point. At least one bearing point or both bearing points can be a point of articulation, for example. A moving point of articulation can be particularly advantageous, which can move, for example, within a guide section when the second handle part is moved from an open position into a closed position and vice versa. The guide section can be configured, for example, as an elongated hole, in particular as a straight or a curved elongated hole, in which an pivot axis is guided that is movable in at least two degrees of freedom and moves along the guide section. For example, the bearing point or points of the drive element on the first handle part and/or on the second handle part can be arranged offset as relates to a point of articulation, for example the already mentioned point of articulation, of at least one of the guide elements on the first handle part and/or on the second handle part. The drive element can be designed, for example, as a drive lever. In order to achieve particularly good power transmission through the drive lever, it can be designed to be stiff, that is to say, in particular, to be inflexible.

In order to configure the largest possible stroke of the surgical instrument with the smallest possible distance between the handle parts, it can be provided according to a further embodiment that at least one of the guide elements and/or a drive element, for example the aforementioned drive element, has a bend. It can be particularly advantageous if the at least one guide element and/or the drive element is inclined in the direction of the first and/or of the second handle part.

According to one refinement, the surgical instrument can have a shaft with a guide rail and a slide rail that can be adjusted relative to the guide rail, with a force transmission being exerted onto the slide rail of the shaft from at least one guide element and/or from a drive element, for example the drive element already mentioned, when the second handle part is actuated. In particular, the shaft can be a cutting and/or punching tool. A stroke of the surgical instrument can thus relate to a maximum relative displacement path between the slide and the guide rail.

In order to achieve an adjustment of a part of a shaft inserted into the shaft receptacle that is as straight as possible or precisely straight, it can be advantageous if the surgical instrument has a compensation device in which an engagement pin engages and establishes contact with an impingement surface of the compensation device, in which a circular movement of the engagement pin is converted or can be converted into a linear movement of the compensation device when the second handle part is actuated. For example, this is in such a way that a contact point of the engagement pin on the impingement surface moves in a direction transverse or perpendicular to the linear movement along the impingement surface. The compensation device can be formed, for example, on a slide rail of the surgical instrument. The engagement pin can be formed, for example, on the drive element.

In order to determine an adjustment of the compensation device along a straight direction of displacement, the compensation device can be firmly connected to a or the slide rail. In this context, firmly connected can in particular mean non-adjustable in an opening angle. In particular, the compensation device can be designed in such a way that an angle between the impingement surface and the slide rail remains unchanged during operation of the surgical instrument. This allows a particularly efficient transmission of hand force, since the hand force can be converted almost completely into a straight adjustment force or is converted during an actuation process.

According to a further embodiment, a plunging recess for plunging at least one guide element in the first and/or the second handle part can be formed on the first handle part and/or on the second handle part. It is thus possible to make the actuation path between the handle parts as large as possible without having to increase the distance between the handle parts. In the closed position, the guide elements and/or the drive element penetrate into the plunging recess(es) such that the handle parts can be moved as close as possible to one another. This has the advantage that the stroke of the surgical instrument can be made even larger.

In order to avoid resetting the handle parts into the open position by hand force, the surgical instrument can, according to a further embodiment, have a resetting element, for example a resetting spring, the resetting force of which counteracts a relative movement of the first handle part towards the second handle part. In order to provide reliable guidance and mounting of the resetting element, a resetting element receptacle, into which the resetting element is inserted, can be formed on one of the guide elements. For example, the resetting element can be designed as a leg spring, the center of rotation of which is formed at a point of articulation of one of the guide elements on the first handle part and/or overlaps therewith.

In order to keep the distance between the two handle parts as small as possible in the open position and/or in the closed position, two contact surfaces, in particular having different orientations, can be formed on the guide elements, with a first pair of contact surfaces of the two guide elements resting against one another in a maximum open position and a second pair of contact surfaces resting against one another in a maximum closed position.

According to one embodiment, a bearing point, for example the aforementioned bearing point, of a drive element, for example the aforementioned drive element, can be arranged on the first handle part further away from a shaft receptacle, for example the shaft receptacle already mentioned, and/or from a shaft, for example the shaft already mentioned, than the points of articulation of the guide elements on the first handle part. A particularly large stroke can thus be configured.

In order to reduce the space requirement of a drive element, for example the drive element already mentioned above, the drive element can be arranged at least partially in a recess in a guide element. The drive element can thus at least partially penetrate into the guide element at the recess. The guide element with the recess can flank the drive element at least partially laterally and/or on both sides.

In order to make it easier for a person with relatively small hands to grasp and operate the surgical instrument, a free end of the second handle part can be inclined in the direction of the first handle part in the rest position. Alternatively or additionally, the free end of the second handle part can be closer, in the rest position, to the first handle part than a handle center point of the second handle part.

In order to reuse the surgical instrument, it can be advantageous if the instrument is made of an autoclavable material or materials. This means that the instrument can be sterilized at temperatures above 120° C. For example, the surgical instrument can be made from one metal or several metals.

In order to increase the stroke of the surgical instrument even further without the distance between the two handle parts having to be increased, it can be provided according to a further embodiment that a pivot axis recess is formed on at least one guide element. If the second handle part is moved towards the first handle part, the guide part with the pivot axis recess can be brought particularly close to the pivot axis of the drive element on the second handle part in the closed position, since the pivot axis of the drive element penetrates into the pivot axis recess.

The invention also relates to a use of a surgical instrument, as described and claimed herein, for moving a cutting and/or punching tool. This enables the surgical instrument to be handled in a particularly force-saving manner, as has already been explained in detail above.

The invention will now be described in more detail using an exemplary embodiment, but is not limited to this exemplary embodiment. Further exemplary embodiments result from the combination of the features of individual or several claims with one another and/or with one or more features of the exemplary embodiment.

BRIEF DESCRIPTION OF THE DRAWINGS

The following is shown:

FIGS. 1 to 8 shown a possible embodiment of a surgical instrument, which is designated overall as 1.

Figure 1:
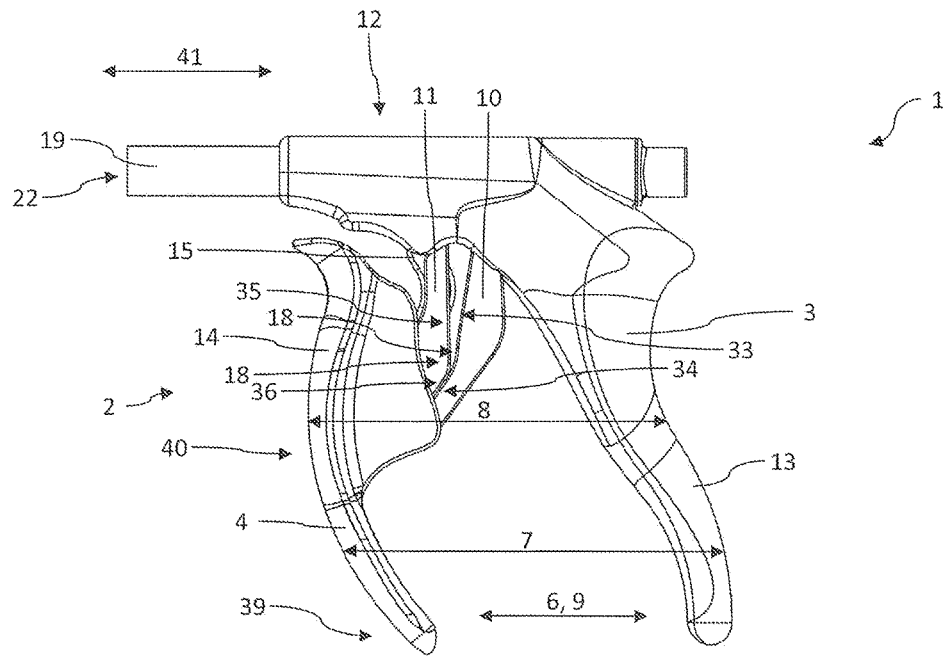
FIG. 1 is a side view of a possible embodiment of the surgical instrument according to the invention, the instrument being shown in an open position, i.e. in the rest position.

The surgical instrument 1 has a grip area 2 which enables a user to hold and operate the surgical instrument 1.

DETAILED DESCRIPTION

The grip area 2 has a first handle part 3 and a second handle part 4. The first handle part 3 is designed as a fixed handle part, that is to say it is held in place by the user when in use. The second handle part 4 is movably mounted, so that it can be adjusted by the user relative to the first handle part 3 along an adjustment direction in the position of use. When the second handle part is actuated while the surgical instrument 1 is in use, the second handle part 4 moves in the direction of the first handle part 3.

At least two points of articulation 5, 17 arranged offset to one another are formed on the second handle part 4, by means of which the adjustment direction 6 of the second handle part 4 is fixed relative to the first handle part 3, since the second handle part 4 is arranged to be movable about both points of articulation 5.

The design of the two points of articulation 5, 17 on the second handle part 4 makes it possible to avoid a pure rotational movement of the second handle part 4 about a single pivot axis. This enables better hand force transmission. The second handle part 4 is moved towards the first joint part 3 by being actuated rather by pivoting about both points of articulation 5, 17.

The aforementioned adjustment direction 6 of the second handle part 4 in the direction of the first handle part 3 is defined by at least two guide elements 10, 11. The first guide element 10 is connected to the first handle part 3 via a point of articulation 5 and to the second handle part 4 via a point of articulation 5. The second guide element 11 is connected to the first handle part 3 via a point of articulation 5 and to the second handle part 4 via a point of articulation 5.

The point of articulation 5 of the first guide element 10 and the point of articulation 5 of the second guide element 11 are each arranged offset to one another on the first handle part 3. The point of articulation 5 of the first guide element 10 and the point of articulation 5 of the second guide element 11 are also each arranged offset from one another on the second handle part 4.

The points of articulation 5 can be, for example, pivot axes guided in a pivot bearing.

Figure 2:
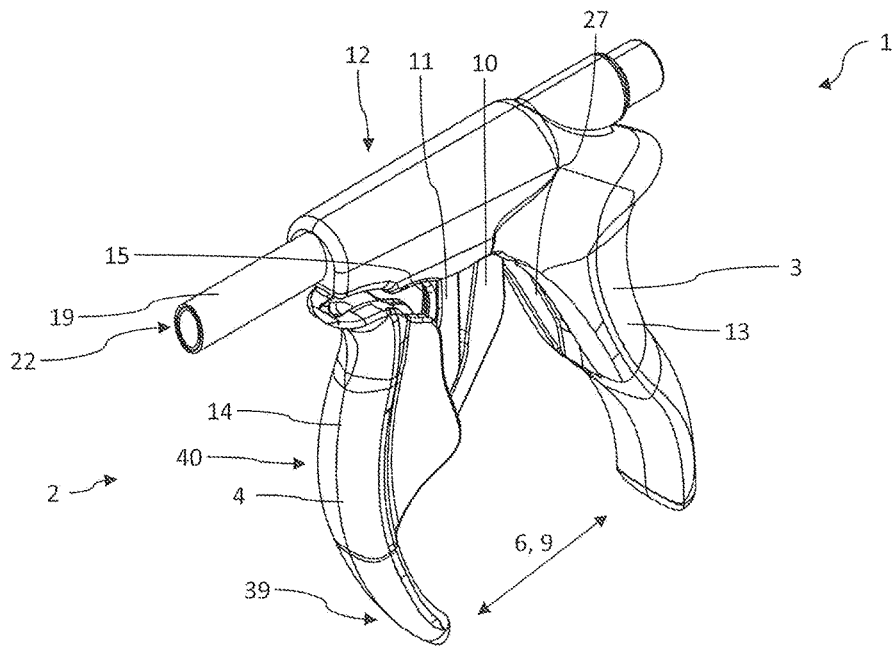
FIG. 2 is a perspective view of the surgical instrument from FIG. 1.
Figure 3:
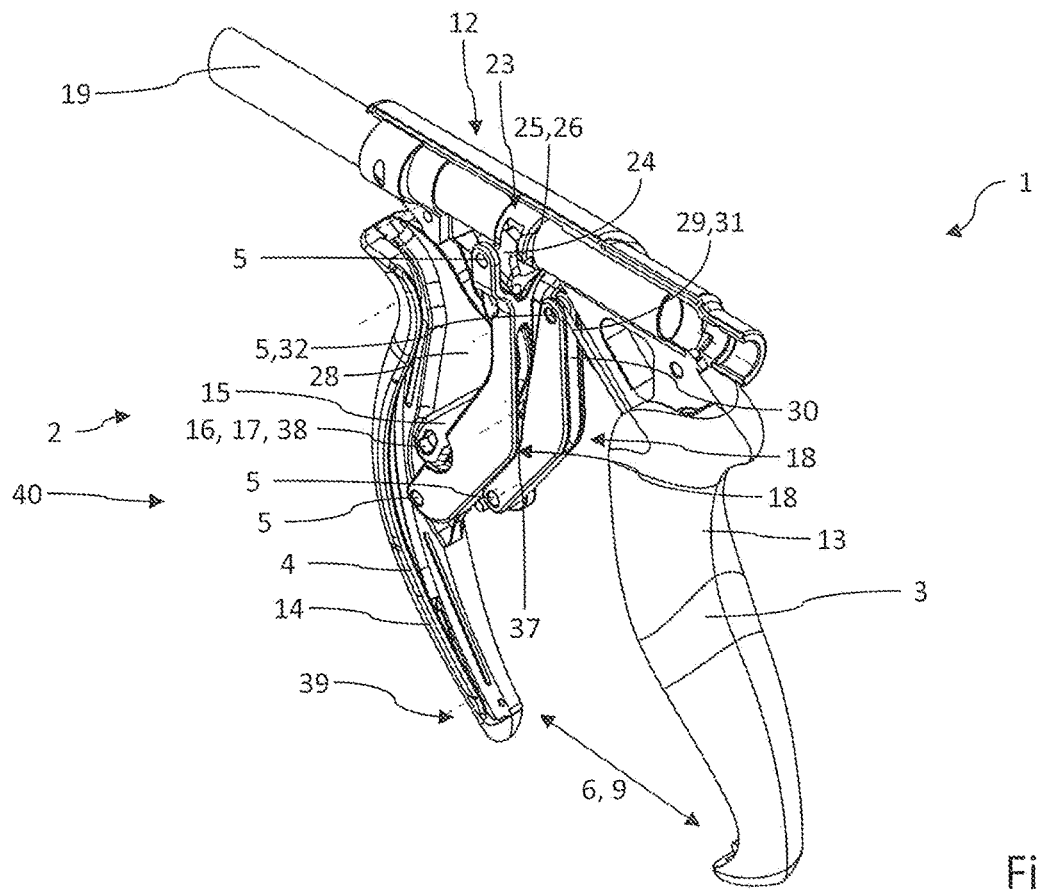
FIG. 3 is an isometric view of the surgical instrument from the aforementioned figures, with a partially open housing.
Figure 4:
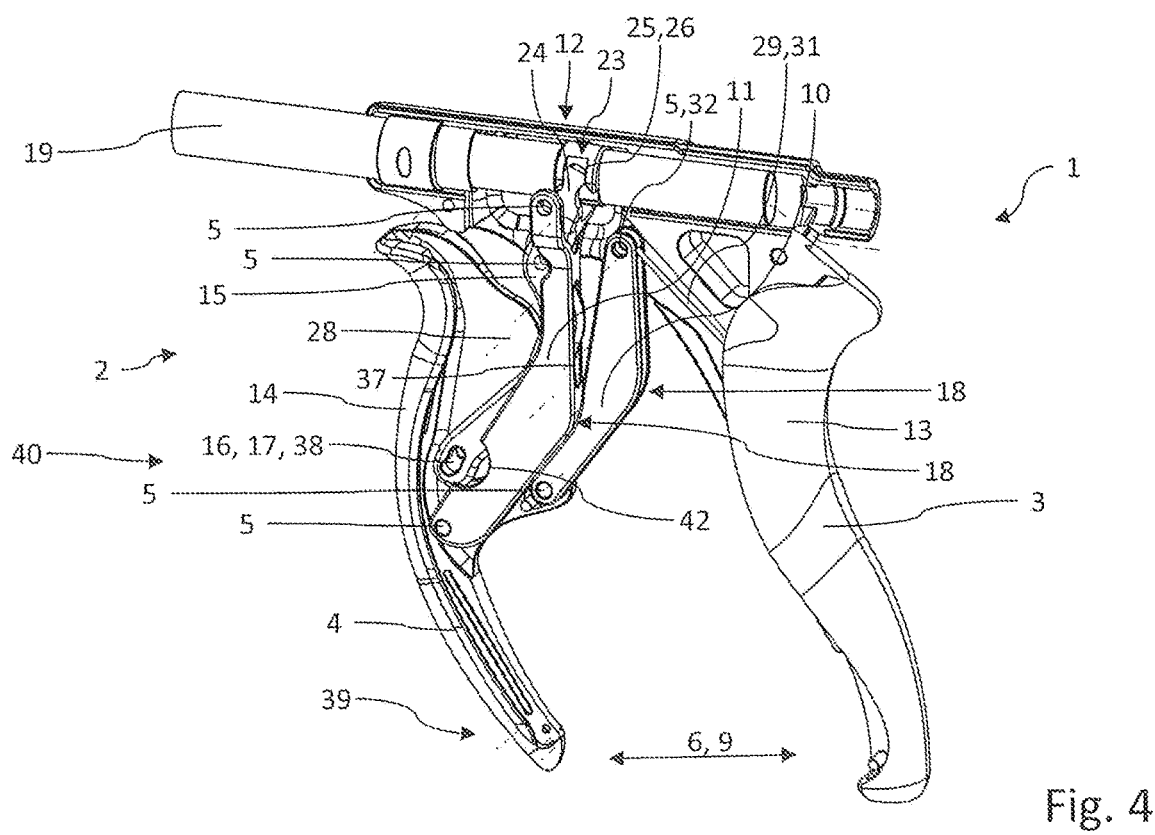
FIG. 4 is another isometric view of the surgical instrument from FIG. 3.
Figure 5:
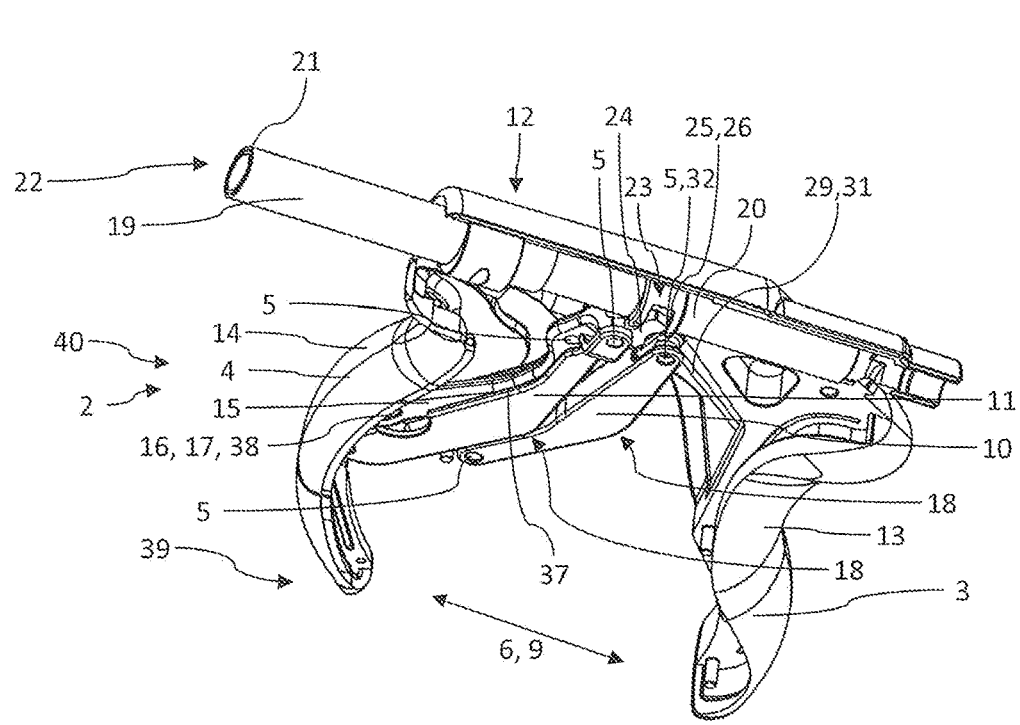
FIG. 5 is another isometric view of the surgical instrument from FIGS. 3 and 4.
Figure 6:
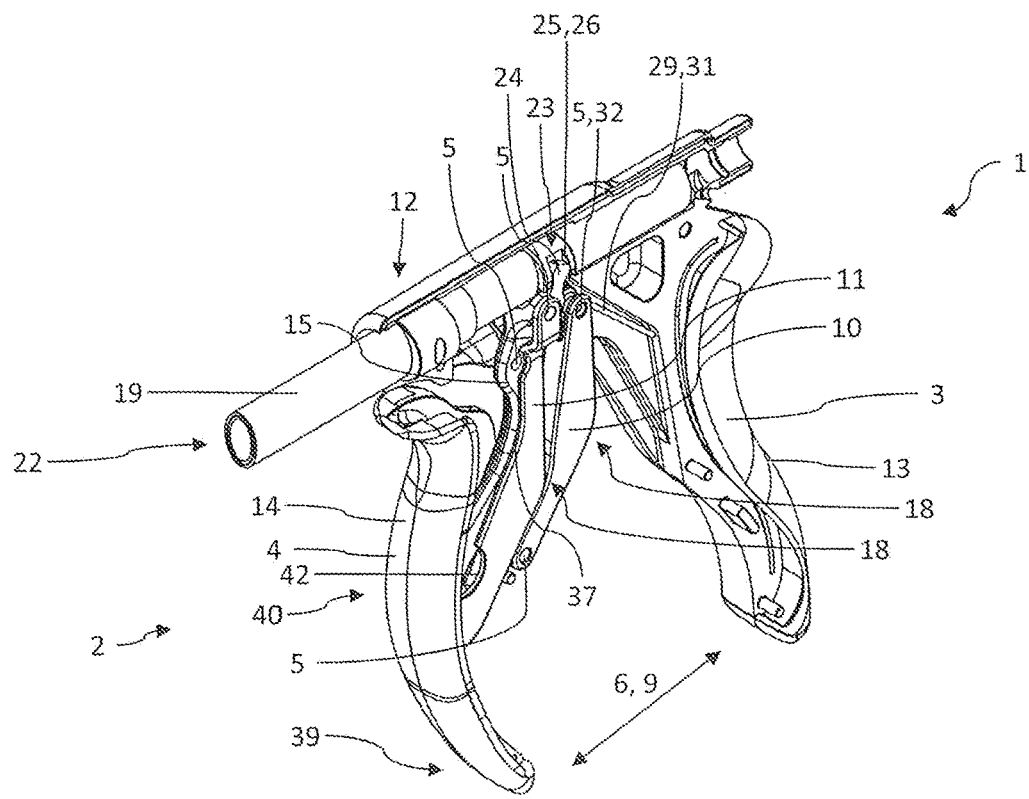
FIG. 6 is another isometric view of the surgical instrument from the aforementioned figures.
Figure 7:
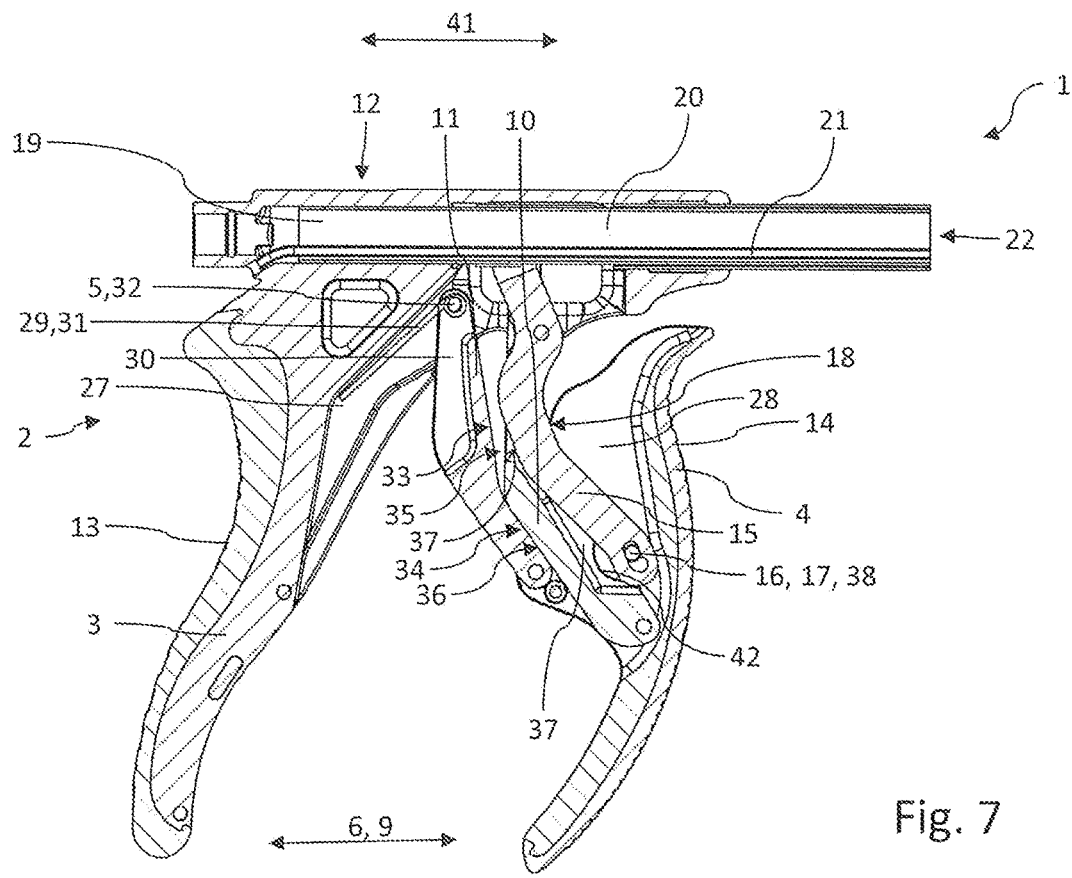
FIG. 7 is a sectional view of the surgical instrument from the aforementioned figures.
Figure 8:
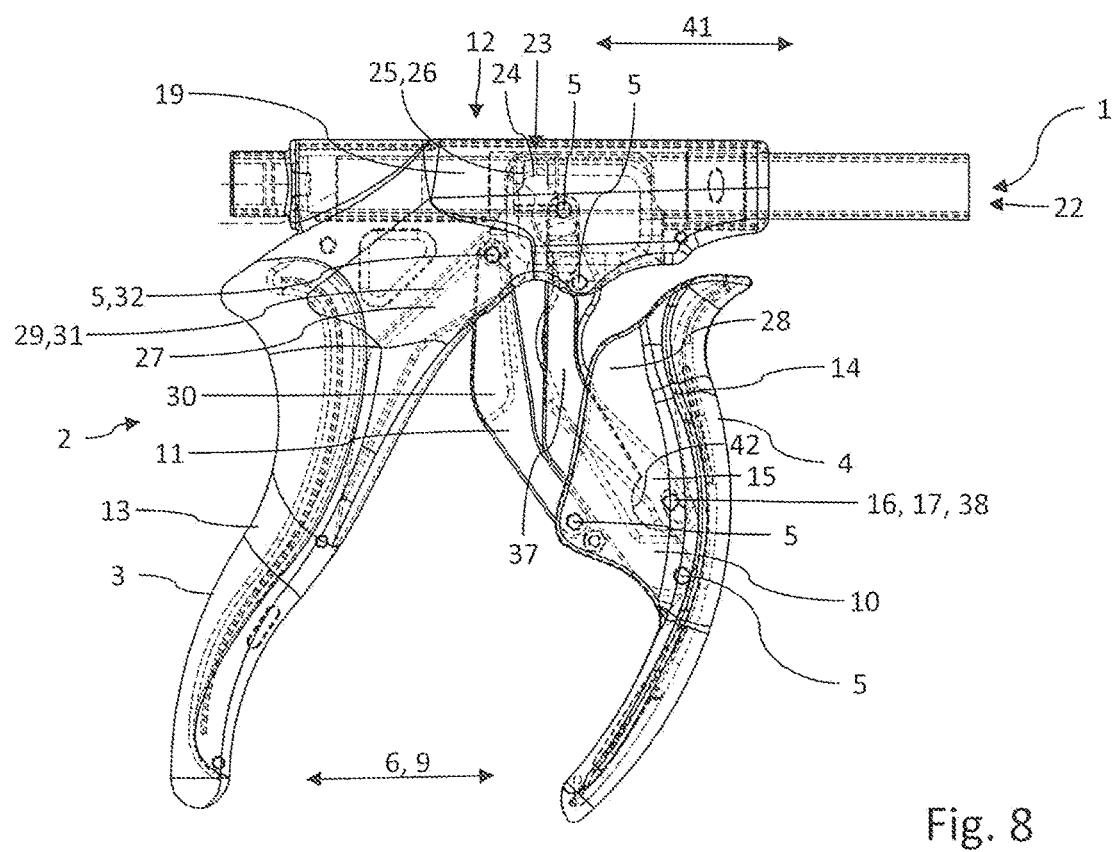
FIG. 8 is a side view of a partially transparently illustrated surgical instrument from the aforementioned figures.

The surgical instrument 1 according to FIGS. 1 to 8 also has a drive element 15 which is connected to the second handle part 4 via a bearing point 16. As shown in FIGS. 3 to 8, the bearing point 16 can be designed, for example, as a point of articulation 17 with a moving pivot axis. The pivot axis can be arranged, for example, in a guide section designed as an elongated hole 38. The second end of the drive element 15 is connected to the first handle part 3 via a point of articulation 5.

However, configurations are also conceivable in which the drive element 15 is supported via two bearing points 16, for example with respectively moving pivot axes, and connected to the handle parts 3, 4. By designing a moving pivot axis, the overall stroke of the surgical instrument 1 can be increased even further without a distance between the two handle parts 3, 4 having to be increased. With the surgical instrument 1 shown in FIGS. 3 to 8, the pivot axis mounted in the guide section designed, for example, as an elongated hole 38 can move from a first, particularly upper, end position in the open position of the surgical instrument 1 to a second, particularly lower, end position in a closed position of the surgical instrument.

The bearing point 16 of the drive element 15 on the second handle part 4 is arranged offset from the points of articulation 5 of the two guide elements 10, 11 on the second handle part 4. Thus, by means of the drive element 15, a significantly larger actuation path 9, which makes up the stroke of the surgical instrument 1, can be achieved.

The two guide elements 10, 11 and the drive element 15 each have a bend 18. As can be seen in FIGS. 1 to 8, the guide elements 10, 11 and/or the drive element 15 can incline in the direction of the second handle part 4 due to the bend 18.

The surgical instrument 1 also has a shaft 19 which is arranged in the shaft receptacle 12 already mentioned above. The shaft 19 comprises a guide rail 20 and a slide rail 21 which can be adjusted relative to the guide rail 20. The slide rail 21 can be designed to be movable relative to the stationary guide rail 20, for example. The guide rail 20 can be firmly connected to the first handle part 3, in particular in such a way that no relative movement is possible between the first handle part 3 and the guide rail 20 in the position of use.

When the second handle part 4 is actuated, power can be transmitted from the drive element 15 to the slide rail 21 of the shaft 19.

In order to prevent the slide rail 21 from lifting off the guide rail 20, which can be caused by a circular movement of the drive element 15, the surgical instrument 1 has a compensation device 23. The compensation device 23 comprises a receiving space with an impingement surface 25. An engagement pin 24 is inserted into the receiving space of the compensation device 23 and makes contact with the impinging surface 25 at a contact point 26. A direction of insertion into the receiving space of the compensation device 23 is preferably aligned perpendicular to a preferably straight-line adjustment movement 41 of the compensation device 23. By actuating the second handle part 4, the contact point 26 of the engagement pin 24 moves along the impingement surface 25 obliquely or perpendicular to the preferably straight adjustment direction 41 of the compensation device 23. This enables a power transmission from the drive element 15 to the impingement surface 25. A rotational movement of the engagement pin 24 can thus be converted into a linear movement 41 of the compensation device 23.

The compensation device 23 is firmly connected to the slide rail 21, so that the slide rail 21 together with the compensation device 23 can be adjusted along the preferably straight direction of displacement 41 by actuating the second handle part 4.

An angle between the impingement surface 25 and the slide rail 21 and/or an angle between the impingement surface 25 and the direction of displacement 41 remains unchanged during an actuation of the second handle part 4. Only the contact point 26 of the engagement pin 24 with the impingement surface 25 and/or the alignment of the engagement pin 24, in particular within the compensation device 23, can change during an actuation of the second handle part 4. The engagement pin 24 can have a preferably cylindrical head part with a round cross-section, via which head part the engagement pin 24 establishes the contact point 26 due to impact of the impingement surface 25 therewith.

In order to keep the distance between the two handle parts 3 and 4 as small as possible, a plunging recess 27, 28 is formed on the first handle part 3 and on the second handle part 4. In the closed position, that is to say when a distance between the first handle part 3 and the second handle part 4 is the smallest, the guide elements 10, 11 and/or the drive element 15 plunge into the plunging recesses 27, 28 on the first handle part 3 and on the second handle part 4.

In order to reset the surgical instrument 1 from its closed position back to its open position, i.e. into the position in which the first handle part 3 and the second handle part 4 are at a maximum distance from one another, without applying manual force, the surgical instrument 1 has a resetting element 29. A resetting force of the resetting element 29 counteracts a closing movement of the surgical instrument 1.

In order to achieve a particularly secure mounting of the resetting element 29, a resetting element receptacle 30, into which the resetting element 29 is inserted, is formed on the first guide element 10.

The first guide element 10 is supported against the first handle part 3 by the resetting element 29. As shown in FIGS. 1 to 8, the resetting element 29 can be designed, for example, as a spring, in particular as a leg spring 31. As can be clearly seen in FIGS. 3 to 8, the center of rotation of the leg spring 31 can correspond to the point of articulation 5 of the first guide element 10 on the first handle part 3 or overlap therewith.

The first guide element 10 has an upper contact surface 33 and a lower contact surface 34. The second guide element 11 has an upper contact surface 35 and a lower contact surface 36. In the open position of the surgical instrument 1, the two contact surfaces 34 and 36 are in contact with one another. In the closed position, the two contact surfaces 33 and 35 rest against one another.

The point of articulation 5 of the drive element 15 on the first handle part 3 is further away from the shaft receptacle 12 and/or arranged on the shaft 19 as the points of articulation 5 of the guide elements 10, 11 on the first handle part 3. Thus, the lever of the drive element 15, which acts on the compensation device 23, is formed to be as long as possible in order to achieve a largest possible stroke of the surgical instrument 1.

The drive element 15 is arranged at least partially in a recess 37 on the second guide element 11. The second guide element 11 thus flanks the drive element 15 at least partially laterally due to its split design with one part each.

In the rest position, a free end 39 of the second handle part 4 is inclined in the direction of the first handle part 3, so that an actuation path 9 for the little finger of a hand to be placed near or on the free end 39 is kept as small as possible.

The free end 39 of the second handle part 4 is thus closer to the first handle part 3 in a rest position, i.e. an open position, than a handle center point 40 of the second handle part 4. The handle center point 40 is arranged on approximately half the distance of the hand contact surface 14 on the second handle part 4.

A pivot axis recess 42 is formed on the second guide element 11, into which pivot axis recess the pivot axis of the bearing point 16 of the drive element 15 engages in the closed position of the surgical instrument 1.

The first handle part 3 is bent, for example, on a hand contact surface 13, that is, it is not designed in a straight line. In particular, the first handle part 3 has an S-shape. A palm recess can be formed on the hand contact surface 13 of the first handle part 3.

The second handle part 4 is designed to be curved on a hand contact surface 14, for example. In particular, the second handle part 4 has a C-shape or an S-shape.

The surgical instrument described and claimed herein is particularly suitable for moving a cutting and/or punching tool 22. The cutting and/or punching tool 22 can, for example, be connected to the slide rail 21, as indicated in FIGS. 1 to 8.

The invention therefore relates in particular to a surgical instrument 1 with a grip area 2, which has a first handle part 3, which is fixed in the position of use, and a second handle part 4, which is movable relative to the first handle part 3 along an adjustment direction 6, in which a ratio between a first distance 7 between the first handle part 3 and the second handle part 4 and a second distance 8 between the first handle part 3 and the second handle part 4 is constant or almost constant during a movement of the second handle part 4 in the direction of the first handle part 3, at least over a portion of the actuation path 9.

The invention claimed is:
1. A surgical instrument for tissue separation comprising:
a grip area which has a first handle part that is fixed in a position of use, and a second handle part which can be moved in an adjustment direction relative to the first handle part; and a shaft with a guide rail and a slide rail adjustable relative to the guide rail;

a compensation device on the slide rail, the compensation device having an impingement surface configured to contact and engage an engagement pin formed on a drive element;

wherein, on the second handle part, a plurality of points of articulation are formed, through which the adjustment direction of the second handle part is defined relative to the first handle part, wherein the adjustment direction of the second handle part is determined by at least two guide levers, each guide lever of the at least two guide levers being connected to the first handle part via at least two points of the plurality of points of articulation and connected to the second handle part via at least another two points of the plurality of points of articulation; and wherein the at least two points of the plurality of points of articulation on the first handle part are arranged offset to each other; and wherein the at least another two points of the plurality of points of articulation on the second handle part are arranged offset to each other; and the surgical instrument includes the drive element which is directly connected to the first and/or second handle part via a bearing point;

wherein, when the second handle part is actuated, force is transmitted from at least one guide lever of the at least two guide levers and/or from the drive element onto the slide rail of the shaft; and wherein when the second handle part is actuated, a circular movement of the engagement pin is converted into a linear movement of the compensation device, such that a contact point of the engagement pin moves on the impingement surface in a direction transverse or perpendicular to the linear movement along the impingement surface.

2. The surgical instrument according to claim 1, wherein the drive element is connected to the first and/or second handle part via a moving pivot axis; and wherein the bearing point of the drive element on the first and/or second handle part is offset to the at least two points of the plurality of points of articulation and/or the at least another two points of the plurality of points of articulation of at least one guide lever of the at least two guide levers on the first and/or second handle part.

3. The surgical instrument according to claim 1, wherein at least one guide lever of the at least two guide levers and/or the drive element is inclined in a direction of the first and/or second handle part.

4. The surgical instrument according to claim 1, wherein the compensation device is connected to the slide rail in a fixed manner such that an angle between the impingement surface and the slide rail remains unchanged during an actuation of the surgical instrument.

5. The surgical instrument according to claim 1, wherein a plunging recess for plunging at least one guide lever of the at least two guide levers into the first and/or second handle part is formed on the first and/or second handle part.

6. The surgical instrument according to claim 1, wherein the surgical instrument has a resetting element, a resetting force of which counteracts a relative movement of the first handle part toward the second handle part; and wherein the resetting element is inserted into a resetting element receptacle formed on one of the at least two guide levers.

7. The surgical instrument according to claim 1, wherein a plurality of contact surfaces, in particular having different orientations, are formed on the at least two guide levers, wherein a first pair of contact surfaces rest against one another in a maximum open position and a second pair of contact surfaces rest against one another in a maximum closed position.

8. The surgical instrument according to claim 1, wherein the bearing point of the drive element on the first handle part is arranged further away from a shaft receptacle and/or from the shaft than the at least two points of the plurality of points of articulation of the at least two guide levers on the first handle part.

9. The surgical instrument according to claim 1, wherein the drive element is arranged at least partially in a recess in a guide lever of the at least two guide levers.

10. The surgical instrument according to claim 1, wherein a free end of the second handle part is inclined in a direction of the first handle part in a rest position such that the free end of the second handle part is closer to the first handle part than to a handle center point of the second handle part in the rest position.

\* \* \* \* \*